(12) United States Patent
Sullivan et al.

(10) Patent No.: US 6,175,027 B1
(45) Date of Patent: Jan. 16, 2001

(54) SYNTHESIS OF BIS (ALKYL CYCLOPENTADIENYL) METALLOCENES

(75) Inventors: Jeffrey M. Sullivan, Loveland; Richard D. Crawford, Longmont, both of CO (US); Albert A. Hummel, Silver Spring, MD (US)

(73) Assignee: Boulder Scientific Company, Mead, CO (US)

( * ) Notice: Under 35 U.S.C. 154(b), the term of this patent shall be extended for 0 days.

(21) Appl. No.: 09/373,735

(22) Filed: Aug. 13, 1999

Related U.S. Application Data

(63) Continuation-in-part of application No. 09/322,927, filed on Jun. 1, 1999, now abandoned.

(51) Int. Cl.⁷ .............................. C07F 17/00; C07F 7/00; C07C 2/02
(52) U.S. Cl. .................... 556/53; 585/375; 260/665 G
(58) Field of Search .................. 556/53; 585/375; 260/665 G

(56) References Cited

U.S. PATENT DOCUMENTS

| 5,474,716 | * | 12/1995 | Lisowsky | 260/665 G |
| 5,831,106 | * | 11/1998 | Langhauser et al. | 512/11 |
| 5,877,366 | * | 3/1999 | Birmingham | 585/354 |

OTHER PUBLICATIONS

Reimschneider, Von R., Zeitschrift Fur Naturforschung, vol. 18b, No. 8, pp. 641–645, Aug. 1963.*

* cited by examiner

*Primary Examiner*—Porfirio Nazario-Gonzalez
(74) *Attorney, Agent, or Firm*—Edward S. Irons

(57) ABSTRACT

A method for producing an alkyl cyclopentadiene by reacting cyclopentadienyl Grignard with an alkyl halide and for converting the alkyl cyclopentadiene to a bis(n-alkyl cyclopentadienyl) Group IV metal dihalide is described.

12 Claims, No Drawings

SYNTHESIS OF BIS (ALKYL CYCLOPENTADIENYL) METALLOCENES

This application is a continuation-in-part of U.S. application Ser. No. 09/322,927 filed Jun. 1, 1999, now abandoned.

FIELD OF THE INVENTION

This invention relates to the synthesis of alkyl cyclopentadienes and to the conversion thereof to bis(alkyl cyclopentadienyl) metallocenes.

BACKGROUND OF THE INVENTION

It is known to produce bis(n-alkyl cyclopentadienyl) metallocenes by reaction of alkyl cyclopentadienyl lithenides with Group IV metal tetrahalides.

It is also known to react a cyclopentadienyl Grignard in ether with allyl bromide or tert.butyl bromide. See, e.g., *Metallocenes,* Wiley-VCH, Vol. 1, 469–47 (1998), citing Riemschneider, R. Z., *Naturforsch.* (1963) 18:641–645.

SUMMARY OF THE INVENTION

Pursuant to this invention, a cyclopentadienyl or a substituted cyclopentadienyl Grignard synthesized in tetrahydrofuran (THF) is added to a refluxing THF solution of an n-alkyl halide. The reaction is quenched with aqueous lower fatty acid, preferably acetic acid, to produce a reaction mixture from which an n-alkylated cyclopentadiene may be separated in good yield, e.g., 70% to 80%. The n-alkylated cyclopentadiene may be converted through an alkali metallide to a Group IV metallocene in a 60% to 70% yield.

Alkyl halides useful in this invention are selected to provide the desired alkyl substituted cyclopentadiene. Preferably, alkyl halides of the formula RX, in which R equals $C_1$ to $C_6$ alkyl and X is a halogen, are used. All substituted cyclopentadienes which may be converted to Grignard compounds are useful in the invention. Cyclopentadienes having one to four ring positions substituted by alkyl groups are appropriate.

DETAILED DESCRIPTION OF THE INVENTION

General Description of Cyclopentdienyl Grignard Synthesis

Syntheses of cyclopentadienyl Grignard reagents are described in *Ann. Chem.* (1915) 4:56, 71, *Compt. Rend.* (1914) 158:1963, and Riemschneider, R. Z., *Naturforsch.* (1963) 18:641–645.

In the preferred practice of this invention, dicyclopentadiene is cracked, e.g., by the method described in U.S. Pat. No. 5,877,366 (Birmingham), to provide cyclopentadiene monomer which is diluted into THF and then passed at THF reflux temperature into a 2 to 4 M, preferably 3 M THF, solution of an alkyl magnesium halide, RMgX, in which R and X are as defined, preferably methyl magnesium chloride. The reaction mixture is agitated under reflux. Unreacted cyclopentadiene is moved by distillation to provide a residual solution of cyclopentadiene Grignard (CpMgX) in THF. The THF concentration in the residual solution may be adjusted to 1 M.

EXAMPLE 1

Exemplification of CpMgCl Synthesis

A first reactor is charged with 165.0 Kg (488.3 moles) of 3.0 M methyl magnesium chloride in THF. The charge is heated to reflux at about 50° C. to 60° C.

A 3 M solution in THF of cyclopentadiene freshly cracked by the method of U.S. Pat. No. 5,877,366 is fed with agitation into the refluxing 3.0 M THF solution of methyl magnesium chloride in the first reactor. After the addition is complete, agitation for about 2 hours is continued at 50–55° C. The pot temperature of the first reactor is then reduced to 25–30° C. under 2–5 psig of nitrogen. The molarity of the resultant THF solution of cyclopentadienyl magnesium chloride (87%) and methyl magnesium chloride (13%) in the first reactor is adjusted to about 0.8 to 1.2, preferably 1.0.

General Description of N-Alkyl Cyclopentadiene Synthesis

A solution of the appropriate bromoalkane in THF is heated to 60–65° C. (reflux) in a reactor. A warm, e.g., 60–65° C., THF solution of cyclopentadienyl Grignard is added under reflux to the contents of the reactor while maintaining the pot temperature at 60–65° C. The consequent reaction is quenched with aqueous acetic acid. The resulting organic layer comprising a THF solution of a n-alkyl cyclopentadiene may be separated and dried, for example, over sodium sulfate.

Any bromoalkane of formula R—Br, in which R is as defined, is useful in the invention to synthesize a corresponding alkyl cyclopentadiene. Any acid having the formula

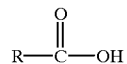

in which R is as defined, may be used in lieu of acetic acid. The aqueous acid quench preferably contains from 10 to 40 weight percent of acid, typically acetic acid. In the preferred practice of the invention, 25 weight percent aqueous acid is used.

EXAMPLE 2

Laboratory Synthesis of n-Butyl Cyclopentadiene

A solution of bromobutane (0.98 mol) in 28 grams of THF is heated to 60–65° C. A warm solution of CpMgCl in THF (1.0 mol) as produced in Example 1 is added to the bromobutane solution while maintaining a pot temperature between 60–65° C. After the addition and the consequent reaction are complete by GC analysis, the reaction mixture is cooled to ambient temperature, 25% by weight of aqueous acetic acid is added, and the organic layer is separated, washed with 10% by weight of aqueous sodium carbonate, and dried over anhydrous sodium sulfate. The organic layer is filtered, and fractionally distilled under reduced pressure to recover 70 to 80% yield of n-butyl cyclopentadiene.

EXAMPLE 3

Pilot Plant Synthesis of N-Butyl Cyclopentadiene

To a 50 gallon stainless steel stirred and jacketed first pressure vessel was added 15.7 kg butyl bromide (114.6 moles) and 10.4 kg THF. The REF is added to aid in mixing and for temperature control at reflux. The mixture was heated via atmospheric steam in the jacket of the vessel to a temperature of 56° C. The reaction vessel is connected to a reflux condenser to return any THF evaporated from the mixture.

63.9 kg (99.6 moles) of 1.56 molar CpMgCl in THF was placed in a 30 gallon glass pressure reaction vessel and heated to 31° C., and resampled to assure that the Grignard was completely dissolved in solution. The molarity titration remained at 1.56 molar. The Grignard solution from the glass pressure vessel was fed into the first pressure vessel while the reaction temperature of the BuBr solution was maintained between 56 and 69° C. (at THF reflux conditions). The feed duration was 2 hours 32 minutes.

10 kg THF was added to rinse the glass pressure reaction vessel and lines clear of any residual Grignard. The reaction mixture in the first pressure vessel was stirred out above 60° C. for 15 minutes, and then was cooled to sample. After confirming complete alkylation and the lack of dibutyl Cp products, an acetic acid quench was started.

To the first pressure vessel was added 5 kg acetic acid and 20 kg water. This mixture was added to the butyl cp/magnesium salt slurry in the first pressure vessel 50 minutes after the feed of CpMgCl was complete. Higher yields and lower dialkyl Cp products are made when the mixture is quenched within an hour after completing the CpMgCl feed. During the acetic acid feed, the temperature ranged from 28° C. and 34° C., with the initial feed very exothermic. The slurry thickened during the feed, and thinned out by the end of the acetic acid feed. The final organic mixture was a clear yellow liquid.

To this mixture was added 500 g NaCl to aid in the density separation of the aqueous from the organic components. The mixture was stirred for 30 minutes, settled for 30 minutes, and the aqueous separated as a clear liquid layer. The organic layer was yellow. There was a slight black rag.

To the organic layer was added 2.5 kg of sodium carbonate, 18.9 kg water, and 100 g of solid caustic. Because the organic mixture was found to be buffered at pH 5, extra base was added to break the buffer to pH 7. the mixture was stirred for 12 hours, settled for 30 minutes, and the lower aqueous layer separated.

To the organic was added 1.1 kg sodium sulfate to dry the mixture. It was stirred for 1 hour, settled for 30 minutes, and filtered through a single can 1 micron filter to a 30 gallon stainless steel pot. The organic was stripped using a packed column setup for reflux return at a 1:1 reflux ratio, under a rough pump vacuum of 20 inches Hg, to remove residual cyclopentadiene from the butyl Cp to a level less than 1% in the pot mixture, as measured by peak area in a Hewlett Packard GC capillary column. The final product is preferably held at a low temperature to minimize dimerization. The final yield of butyl Cp was obtained by proton NMR, for a yield of 28.7 kg of butyl Cp solution, at 21.7% contained, for a net yield of 7.2 kg or 51% conversion from the CpMgCl.

EXAMPLE 4

Pilot Plant Synthesis of N-Propyl Cyclopentadiene

To a first 50 gallon stainless stool agitated jacketed pressure vessel was added 6.5 kg propyl bromide (53 moles) and 7 kg THF. The mixture was heated to reflux to a temperature of 64° C., and feed of CpMgCl as produced by the method of Example 1 was added, titrated to 1.06 molar CpMgCl/MeMgCl in THF, with a CpMgCl constituting 87% of the Grignard. The MeMgCl is an impurity, and not necessary or detrimental for the chemistry. To the first pressure vessel was added 50 kg CpMgCl. The feed duration was 2 hours, 41 minutes.

In a 50 gallon glass receiver vessel was mixed 2.25 kg glacial acetic acid and 9.1 kg water (2.4 gallons). Forty minutes after the CpMgCl fees was complete, the acetic acid mixture was added to the propyl Cp solution in the first pressure vessel. The feed was initially very exothermic, and became thick during the feed. At the end of the feed, the solution became a thin yellow transparent solution.

To this mixture was added 0.5 kg sodium chloride, and the solution stirred for two hours. The solution was settled for 15 minutes, and the lower cloudy aqueous solution separated to a 100 gallon stainless vessel.

To the organic was added 1.4 kg of sodium carbonate, 4.5 kg of sodium chloride, 150 grams of solid sodium hydroxide, and 4.5 kg of water (11.9 gallons). This mixture was stirred for 3 hours, settled for 15 minutes, and the clear bottom aqueous solution separated to the stainless vessel. The mixture of the two aqueous mixtures was extracted with 8 kg of diethyl ether, stirred for 15 minutes, settled for 15 minutes, and the clear aqueous discarded to a plastic drum. The upper organic ether layer was returned to the first pressure vessel.

To this mixture was added 2 kg of sodium sulfate, and the solution was stirred overnight for 10 hrs. The solution was filtered through a 1 micron filter to the 30 gallon stainless steel vessel, where the solution was stripped of ether and residual cyclopentadiene in a packed column equipped with reflux return and at a 1:1 reflux ratio, under a rough pump vacuum of 20 inches Hg. The maximum temperature of the pot was 27° C. After the strip, the concentration of cyclopentadiene in the pot sample was less than 0.5%. Yield was 7.8 kg of propyl cyclopentadiene in THF, at 45.9% concentration, or 33.1 moles of propyl cyclopentadiene contained, for a yield of 72%. The amount of dialkyl substituted product was less than 1% of the propyl cyclopentadiene.

EXAMPLE 5

Description of Bis(N-Alkyl Cyclopentadienyl) Group IV Metal Halide Synthesis

The alkyl cyclopentadiene produced by this invention may be converted in known manner to bis alkyl cyclopentadienyl Group IV metal dihalides. For example, a solution of n-butyl lithium in hexane is fed into a THF solution of an n-alkyl cyclopentadiene. A Group IV metal tetrahalide is added. A reaction mixture comprising bis(n-alkyl cyclopentadienyl) Group IV metal dihalide is produced.

EXAMPLE 6

Bis(N-Butylcyclopentadienyl) Zirconium Dichloride 113.4 Kg of n-butylcyclopentadiene in THF, containing 22.7 kg of n-butylcyclopentadiene as produced by the method of Example 3 was charged to a clean, dry, nitrogen-purged first reaction and chilled with agitation to a temperature of −25° C. to −15° C.

78.9 kg of 1.6 M n-butyllithium 15% in hexane is charged to the first reactor. The pot temperature is maintained at −15° C. to −25° C. The resulting mixture in the first reactor is stirred for 16 hours during which time the pot temperature is allowed slowly to rise to the range of 20° C. to 25° C. Thereafter, the first reactor pot temperature is reduced to −25° C. to −15° C.

21.6 kg of $ZrCl_4$ are added in 4.5 kg increments over a period of 1 hour. Upon completion of the $ZrCl_4$ addition, the pot temperature of the first reactor is raised to a range of 40° C. to 45° C., and the reaction mixture agitated for 2 hours at that temperature. In a separate vessel, diluted aqueous HCl is prepared by adding 6.3 kg of HCl to 100 kg of water. The aqueous HCl so prepared is added to the contents of the first reactor, while the pot temperature is maintained below 20° C. The resulting mixture is agitated for 10 minutes and allowed to settle for 20 minutes. The resulting upper, organic and lower aqueous layers are separated. The separated organic layer in the first reactor is dried over sodium sulfate. Solvents (THF/hexane) are removed from the dried organic layer by distillation to a pot temperature of 80° C.

181.4 kg of hexane are added, with agitation, to the first reactor. The resulting slurry is filtered. Filtration yields off-white crystalline solid bis(butyl-cyclopentadienyl) zirconium dichloride.

EXAMPLE 7

Synthesis of Bis (Propylcyclopentadienyl) Zirconium Dichloride

Example 6 is substantially repeated with the exception that n-propylcyclopentadiene prepared as described in Example 4 was utilized instead of n-butylcyclopentadiene.

We claim:

1. A method which comprises:
   (i) converting cyclopentadiene or a substituted cyclopentadiene to a Grignard reagent;
   (ii) reacting said step (i) Grignard reagent with an alkyl halide
      wherein a first reaction mixture containing an alkyl cyclopentadiene and magnesium salts is produced; and
   (iii) quenching said step (ii) reaction with aqueous acetic acid
      wherein a second reaction mixture containing said alkyl cyclopentadiene is produced.

2. A method according to claim 1, wherein said step (ii) reactant is n-propyl or n-butyl bromide.

3. A method according to claim 1, further comprising converting said alkyl cyclopentadiene produced in step (iii) to a bis(n-alkyl cyclopentadienyl) Group IV metal dihalide.

4. In a method of synthesizing an alkyl cyclopentadiene by reaction of a cyclopentadiene Grignard with an alkyl halide,
   wherein a reaction mixture containing said alkyl cyclopentadiene is produced,
the improvement which comprises quenching said reaction by treating said reaction mixture with any aqueous acid
   wherein said acid has the formula

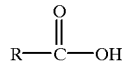

in which R is $C_1$ to $C_6$ alkyl.

5. A method according to claim 4 in which said aqueous acid contains from 10 to 40 weight percent of said acid.

6. The claim 4 or claim 5 method wherein said aqueous acid is aqueous acetic acid.

7. A method according to claim 4 or claim 5 of synthesizing an alkyl cyclopentadiene by reaction of a cyclopentadiene Grignard with an alkyl halide, wherein a reaction mixture containing said alkyl cyclopentadiene is produced, the improvement which comprises introducing said cyclopentadiene Grignard to a refluxing solution of said alky halide in tetrahydrofuran.

8. A method according to claim 4 or claim 7 method in which said alkyl halide is n-propyl bromide or n-butyl bromide.

9. A method for producing a cyclopentadienyl Grignard which comprises:
   (i) cracking dicyclopentadiene to produce cyclopentadiene monomer,
   (ii) passing said cyclopentadiene monomer produced in step (i) directly into tetrahydrofuran at reflux temperature, wherein a solution of cyclopentadiene in tetrahydrofuran produced, and
   (iii) combining said step (ii) tetrahydrofuran solution with a 2 to 4 molar solution of an alkyl magnesium halide in tetrahydrofuran.

10. A method which comprises
    (i) reacting an alkyl lithium compound with an n-alkyl cyclopentadiene produced by the method of claim 4, wherein a first reaction mixture containing a lithenide of said n-alkyl cyclopentadiene is produced, and
    (ii) treating said step (i) first reaction mixture with a Group IV metal tetrahalide, wherein a second reaction mixture containing a bis(n-alkyl) cyclopentadienyl Group IV metal dihalide is produced.

11. A method according to claim 10 wherein said step (i) n-alkyl cyclopentadiene is n-propyl or n-butyl cyclopentadiene, and wherein said step (ii) Group IV metal tetrahalide is zirconium tetrachloride or hafnium tetrachloride.

12. A method for producing bis-n-propyl cyclopentadienyl zirconium dichloride which comprises
    (i) adding zirconium tetrachloride to a tetrahydrofuran solution of n-propyl cyclopentadienyl lithium made from n-propyl cyclopentadiene produced by the method of claim 10, wherein a reaction mixture containing said bis-n-propyl cyclopentadienyl zirconium dichloride is produced, and wherein said reaction mixture comprises an organic layer, and
    (ii) separating said step (i) organic layer and washing said separated layer with a weak acid solution and removing solvents therefrom.

* * * * *